United States Patent [19]

Karger et al.

[11] Patent Number: 4,865,707
[45] Date of Patent: Sep. 12, 1989

[54] CAPILLARY GEL ELECTROPHORESIS COLUMNS

[75] Inventors: Barry L. Karger, Newton; Aharon S. Cohen, Brookline, both of Mass.

[73] Assignee: Northeastern University, Boston, Mass.

[21] Appl. No.: 143,442

[22] Filed: Jan. 12, 1988

Related U.S. Application Data

[63] Continuation-in-part of Ser. No. 921,311, Oct. 21, 1986.

[51] Int. Cl.$^4$ ............... G01N 27/28; G01N 27/26
[52] U.S. Cl. ........................ 204/182.8; 204/299 R; 204/180.1
[58] Field of Search ............ 204/180.1, 299 R, 182.8

[56] References Cited

U.S. PATENT DOCUMENTS

| | | | |
|---|---|---|---|
| 3,728,145 | 4/1973 | Hjerten | 117/54 |
| 3,876,775 | 4/1975 | Izaka et al. | 424/177 |
| 4,533,307 | 8/1985 | Ansorge | 204/299 R |
| 4,582,868 | 4/1986 | Ogawa et al. | 524/27 |
| 4,600,641 | 7/1986 | Ogawa et al. | 428/355 |
| 4,657,656 | 4/1987 | Ogawa et al. | 204/299 |
| 4,680,201 | 7/1987 | Hjerten | 204/299 R X |
| 4,690,749 | 9/1987 | Van Alstein et al. | 204/299 R |
| 4,699,705 | 10/1987 | Ogawa et al. | 204/299 |

OTHER PUBLICATIONS

Hjerten, S., "High Performance Electrophoresis: The Electrophoretic Counterpart of High-Performance Chromatography", Journal of Chromatography 270 (1983) 1-6.
S. Hjerten, J. Chromatography, 347, pp. 191-198 (1985).
J. W. Jorgenson & K. D. Lukacs, Clin. Chem., 27, 1553 (1981).
S. Hjerten, Chromatographic Review, 9, 122-129 (1967).
J. Calvin Giddings, Separation Science, 4(3), pp. 181-189 (1969).
Shigeru Terabe, et al., Anal. Chem., 56, pp. 111-113 (1984).
J. W. Jorgenson & K. D. Lukacs, Science, 222, pp. 266-272, (1983).
B. D. Hames & D. Rickwood, Eds., "Gel Electrophoresis of Proteins", IRL Press, Oxford and Washington, D.C., 1981.

Primary Examiner—John F. Niebling
Assistant Examiner—John S. Starsiak, Jr.
Attorney, Agent, or Firm—Weingarten, Schurgin, Gagnebin & Hayes

[57] ABSTRACT

An improved microcapillary column for high performance electrophoresis includes a microcapillary, a hydrophilic polymer within a gel of crosslinked polyacrylamide polymerized in the tube, and preferably, a thin layer of connecting material covalently bonded to the inner surface of the microcapillary wall and to the polymeric gel. The microcapillary is prepared by first covalently bonding a suitable bifunctional reagent to the inner surface of the microcapillary wall, and then causing a mixture of the hydrophilic polymer, monomer, crosslinking agent, and polymerization catalyst to react in the bore of the microcapillary to form a hydrophilic polymer-containing gel matrix which is covalently bonded to the microcapillary wall via the bifunctional reagent. In electrophoresis, this improved gel-containing microcapillary can provide peak efficiencies in excess of 100,000 theoretical plates within separation times of less than thirty minutes, permits trace level determinations of molecular weights, and permits electrophoretic operation at fields of 1000 V/cm or higher, resulting in extremely high resolution separations.

40 Claims, 4 Drawing Sheets

CAPILLARY GEL ELECTROPHORESIS COLUMNS

This application is a continuation-in-part of application Ser. No. 921,311, filed Oct. 21, 1986.

FIELD OF THE INVENTION

This invention relates to electrophoresis, and more particularly to gel-containing microcapillary columns for high performance electrophoresis.

BACKGROUND OF THE INVENTION

Electrophoresis is one of the most widely used separation techniques in the biologically-related sciences. Molecular species such as peptides, proteins, and oligonucleotides are separated by causing them to migrate in a buffer solution under the influence of an electric field. This buffer solution normally is used in conjunction with a low to moderate concentration of an appropriate gelling agent such as agarose or polyacrylamide to separate analytes by size and to minimize the occurrence of convective mixing.

Two primary separating mechanisms exist, separations based on differences in the effective charge of the analytes, and separations based on molecular size. The first of these mechanisms is limited in the case of separations of oligonucleotides because in the high molecular weight range the effective charges of these materials become rather similar, making it difficult or impossible to separate them. In the case of proteins, charge and size can be used independently to achieve separations. Separations based on molecular size are generally referred to as molecular sieving and are carried out employing as the separating medium gel matrices having controlled pore sizes. In such separating systems, if the effective charges of the analytes are the same, the separation results from differences in the abilities of the different sized molecular species to penetrate through the gel matrix. Smaller molecules move relatively more quickly than larger ones through a gel of a given pore size. Oligonucleotides and medium to high molecular weight polypeptides and proteins are commonly separated by molecular sieving electrophoresis. In the case of proteinaceous materials, however, it is first necessary to modify the materials to be separated so that they all have the same effective charges. This is commonly done by employing an SDS-PAGE derivatization procedure, such as is discussed in "Gel Electrophoresis of Proteins," B. D. Hames and D. Rickwood, Eds., published by IRL Press, Oxford and Washington, D.C., 1981. The contents of this book are hereby incorporated herein by reference.

Sometimes it is desirable to separate proteinaceous materials under conditions which pose a minimal risk of denaturation. In such cases system additives such as urea and SDS are avoided, and the resulting separations are based on differences in both the molecular sizes and charges Most electrophoretic separations are today conducted in slabs or open beds. However, such separations are hard to automate or quantitate. Additionally, polyacrylamide gel layers are known to be rather fragile and easily broken. To impart elasticity to such gel layers and to control viscosity, Ogawa has employed water-soluble polymeric additives such as poly(vinyl alcohol), poly(vinyl pyrrolidone), polyacrylamide, polyethylene glycol and polypropylene glycol. See, for example, U.S. Pat. Nos. 4,699,705; 4,657,656; 4,600,641; and 4,582,686. A further problem with flat gel layers for electrophoresis is that they suffer from Joule heating effects under high fields.

Extremely high resolution separations of materials having different effective charges have been achieved by open tubular free-zone electrophoresis and isotachophoresis in narrow capillary tubes. In addition, bulk flow can be driven by electroosmosis to yield very sharp peaks. Such open tubular electrophoresis is not applicable to the separation of medium to high molecular weight oligonucleotides, however, since these materials have very similar effective charges, as indicated above. In addition, open tubular electrophoresis does not provide size selectivity for proteinaceous materials. The questions thus arise whether electrophoresis on gel-containing microcapillaries can be employed to achieve high resolution separations of oligonucleotides, whether non-denaturing gels in such microcapillaries can be used to separate proteinaceous materials, and whether the conventional procedure of SDS-PAGE can be accomplished on such microcapillaries. As demonstrated by the present disclosure, the answers to these questions are yes, although given its potential importance as a separating technique in the biological sciences, surprisingly little attention has been paid to microcapillary gel electrophoresis. Hjerten has published an article in the *Journal of Chromatography*, 270, 1–6 (1983), entitled "High Performance Electrophoresis: The Electrophoretic Counterpart of High Performance Liquid Chromatography," in which he employs a polyacrylamide gel in tubes having inside dimensions of 50–300 micrometers, and wall thicknesses of 100–200 micrometers. However, this work suffers from limited efficiency and relatively poor performance due in part to the use of relatively wide bore capillaries, relatively low applied fields, and high electrical currents. He has also obtained a patent, U.S. Pat. No. 3,728,145, in which he discloses a method for coating the inner wall of a large bore tube with a neutral hydrophilic substance such as methyl cellulose or polyacrylamide to reduce electroendosmosis.

In microcapillary gel electrophoresis, resolution between two compounds is influenced by all the factors which affect band sharpness, including sample size, ionic materials in the samples, and the gel concentration. The latter factor is especially important, since if the gel concentration is too high the analytes are totally excluded from the column, while if it is too low no molecular sieving occurs. No single gel concentration is optimal for the resolution of all mixtures of proteinaceous materials or oligonucleotides. It is necessary to select appropriate gel concentrations for particular samples. Other important variables affecting electrophoresis in microcapillaries are the applied field and the electrical current employed.

The current employed in microcapillary electrophoresis is proportional to the square of the tube radius, and the power dissipated is proportional to the square of the current employed at a given voltage. To keep heating effects low therefore requires low currents, which in turn implies the need to use tubes having as small a radius as reasonably possible.

Regarding the effect of the applied field on the resolution attainable in capillary electrophoresis, assuming band broadening is due only to axial diffusion, Giddings in *Separation Science*, 4, 181–189 (1969) has derived the equation:

$$R_s = \frac{\Delta\mu E \sqrt{t}}{4\sqrt{2D}}$$

where $R_s$ is the resolution achievable between two components of a mixture, $\Delta\mu$ is the difference in electrophoretic mobility of two consecutive solutes, E is the applied electric field, t is the time for the electrophoretic analysis, and D is the diffusion coefficient of solutes in the medium (generally taken for proteins to be about $10^{-6}$ cm$^2$/sec). As $$t = \frac{L}{E\mu_{ep}}$$

where L is the tubing length from injection to the point of detection and $\mu_{ep}$ is the electrophoretic mobility, substituting in the above equation for t yields $$R_s = \frac{\Delta\mu(EL)^{\frac{1}{2}}}{4(2\mu_{ep}D)^{\frac{1}{2}}}$$

An examination of these equations shows that for the case where band broadening is due to axial diffusion, increasing the applied electric field E should increase the resolution in all circumstances. However, it is elementary that increasing the applied potential also increases the current, which in turn increases the heat which must ultimately be dissipated. Thus in the final analysis, for best resolution one must use the highest applied electric fields consistent with manageable thermal effects. It would therefore be very desirable to have gel-containing microcapillary electrophoresis columns which can tolerate the application of high applied electric fields and which do not suffer from thermal effects produced by such fields.

SUMMARY OF THE INVENTION

Many of the deficiencies of the prior art are overcome and the above-identified needs are answered by the present invention, which provides an improved gel-containing microcapillary for high performance electrophoresis. It includes a microcapillary, a crosslinked polymeric gel containing a hydrophilic polymer such as polyethylene glycol in the interior cavity of the microcapillary, and preferably, a very thin layer of connecting material between the inner surface of the microcapillary wall and the polymeric gel material, this layer of connecting material being covalently bonded both to the microcapillary wall and to the polymeric gel. A preferred microcapillary construction material is fused silica, and a preferred crosslinked polymeric gel material is a copolymer of acrylamide and N,N'-methylenebisacrylamide. The layer of connecting material between the microcapillary wall and the polymeric gel originates as a bifunctional reagent possessing a first reactive functional group capable of reacting with reactive functionalities on the interior surface of the capillary wall, silanol groups for example, and a second reactive group which is capable of reacting with vinyl monomers and crosslinking agents which when polymerized constitute the polymeric gel.

The hydrophilic polymeric additive stabilizes the column of gel against breaks and formation of bubbles, and unexpectedly enables operation of the microcapillary column in very high electric fields (or more exactly, high power) despite the consequent relatively high Joule heating, resulting in very high resolution separations.

The preferred gel-containing microcapillary of the invention, in which the gel is linked to the capillary wall, is prepared in several stages, as follows: first, the interior surface of a microcapillary is contacted with a basic material to activate it, and then this microcapillary is treated with a solution of an appropriate bifunctional reagent capable of covalent bonding to the microcapillary wall and to a polymeric gel to be formed in the microcapillary. Upon treatment of the activated microcapillary with the solution of this bifunctional reagent, a layer of the bifunctional reagent is covalently attached to the inner surface of the microcapillary wall. Following this operation, unreacted bifunctional reagent is removed and then the coated microcapillary is treated with a solution containing a hydrophilic polymer such as polyethylene glycol, at least one monomer, at least one crosslinking agent, and at least one free radical source, and this mixture is allowed to polymerize in the microcapillary tube ultimately forming a crosslinked polymeric matrix which contains the hydrophilic polymer and which is covalently bound to the microcapillary wall via the bifunctional reagent As a final step, one end of the gel-containing microcapillary is cut off cleanly and squarely In the event no bifunctional reagent is employed to bond the gel to the microcapillary wall, the operations relating to bifunctional reagent are omitted and the microcapillary is simply treated with the solution containing hydrophilic polymer, monomer, crosslinking agent, and free radical source, and polymerization carried out as above.

The gel-containing microcapillaries of the invention are unusually stable and function well under applied electric fields typically of 1000 V/cm or higher, and with currents typically to approximately 50 microamperes or above. Under these conditions, very high resolution separations are obtained on very small amounts of material In addition, the microcapillaries of the invention resolve mixtures of analytes as a linear function of the logarithms of their molecular weights. Accordingly, they permit convenient and accurate molecular weight determinations on nanogram or lower amounts of unknown biopolymers.

DESCRIPTION OF THE DRAWING

The invention will be better understood from a consideration of the following detailed description taken in conjunction with the drawing in which.

DETAILED DESCRIPTION OF THE INVENTION

Figure 1:
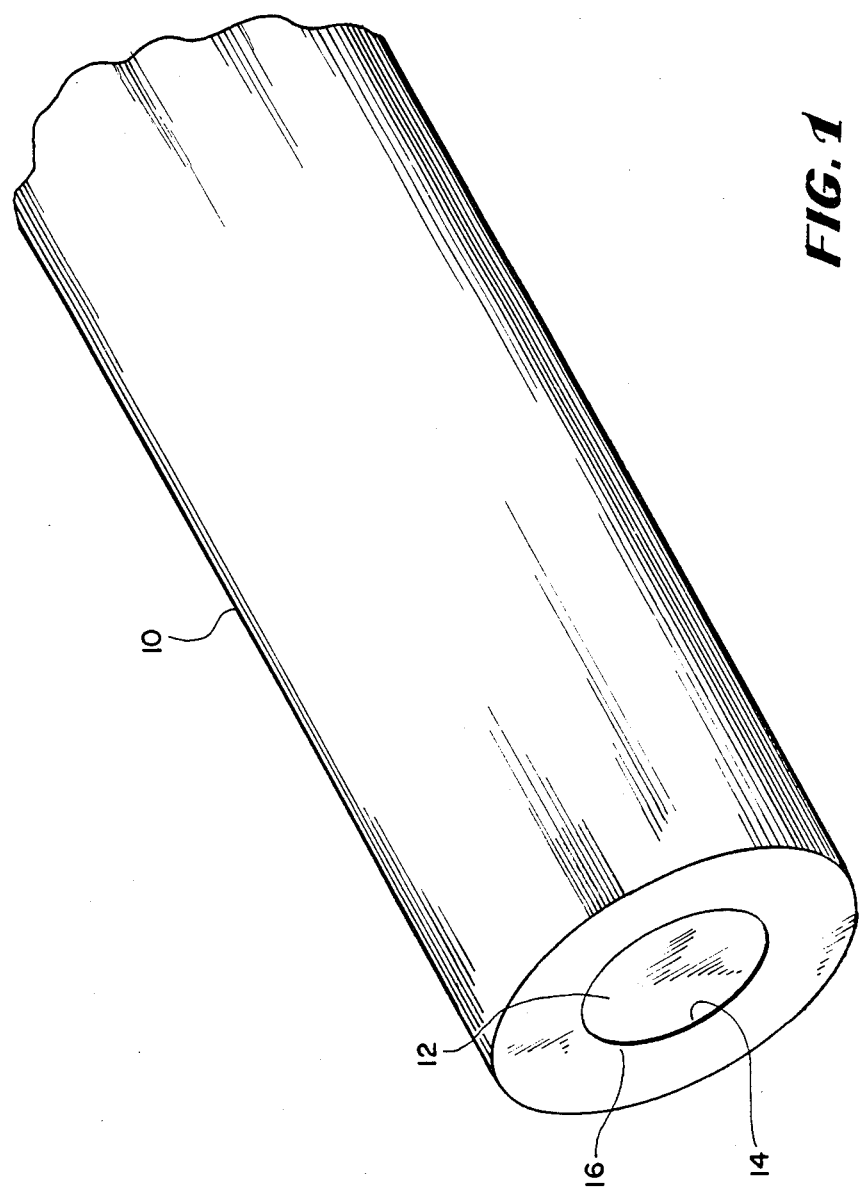
FIG. 1 shows a magnified perspective view of the end of the gel-containing microcapillary of the invention.

As shown in FIG. 1, the improved gel-containing microcapillary column of the invention includes a microcapillary 10, a crosslinked polymeric gel material 12 within the bore of this microcapillary, and preferably, a connecting layer 14 which is covalently bonded to both the polymeric gel 12 and the inner surface 16 of the microcapillary wall. The polymeric gel 12 contains a hydrophilic polymer such as polyethylene glycol.

The microcapillary may be made of any of a variety of materials provided that the detection system to be employed in the electrophoresis can function adequately with the particular material employed Suitable materials include glass, alumina, beryllia, and TEFLON, though not all of these materials will react with the bifunctional reagents which bond the gel to the microcapillary wall in the preferred embodiment of the invention. Preferably, the microcapillary is made of fused silica.

In general, the microcapillary dimensions are important, in two respects—first, as the internal diameter of the microcapillary is reduced, the electric current and the resultant heating produced by a particular applied electric field is reduced, and second, the thinner the microcapillary wall can be made, the better heat transfer from the microcapillary is achieved. Thus, for highest resolution separations it is desirable that the microcapillary have a minimum internal diameter and also a minimal wall thickness. With the improved hydrophilic polymer-containing microcapillaries of this invention, however, these considerations are somewhat less important than formerly, because the improved microcapillaries apparently tolerate heat better than microcapillaries not containing such additives. Accordingly, microcapillaries having an internal diameter range between 10 and 2000 micrometers and a wall thickness in the range 25–400 micrometers work well. A preferred range of internal diameters is 25 to 200 micrometers and a preferred range of wall thickness is 40 to 100 micrometers. Obviously, if the wall thickness is made too small, the microcapillary will be too fragile for practical use. A polyimide coating on the microcapillary permits easy handling of thin-walled microcapillaries.

The polymeric gel material 12 employed can be any cross-linked polymer which has a pore structure which can be varied by varying the amounts of monomer and crosslinking agent and the reaction conditions. Examples of such polymeric systems are polyacrylamide and mixtures of agarose and polyacrylamide. A preferred polymeric gel material is based on acrylamide and $N,N'$-methylenebisacrylamide, the $N,N'$-methylenebisacrylamide serving as a crosslinking agent Other possible crosslinking agents are $N,N'$-(1,2-dihydroxyethylene)-bisacrylamide, $N,N'$-diallyltartardiamide, $N,N'$-cystamine-bisacrylamide, and N-acryloyltris(hydroxymethyl)aminomethane. Other monomers and other crosslinkers will suggest themselves to those skilled in the art.

The polymerization reaction is preferably initiated with ammonium persulfate and $N,N,N',N'$-tetramethyleneethylenediamine, though other free radical polymerization initiators may be employed, as known by those skilled in the art.

The connecting layer 14 preferably employed between the polymeric gel and the inner surface of the microcapillary wall is preferably derived from a bifunctional reagent which is capable of chemically bonding both to the microcapillary wall and to the monomeric or crosslinking agents employed in the polymerization reaction which forms the gel material. This bifunctional reagent is generally a molecular chain having appropriate reactive functional groups at its respective ends, though non-chain type molecules having appropriate functionalities will also serve. One en of the bifunctional reagent carries a reactive functional group which can bond chemically to silanol groups or other reactive functionalities on the inner surface of the microcapillary wall Such reactive functional groups are typically reactive silanes such as trialkoxy silane, trichloro silane, mono, di-, or tri-enolate silanes, and amino silanes, where the silicon atom carries at least one group which may be readily displaced. The opposite end of the bifunctional reagent contains a second reactive functional group capable of forming a covalent bond with the polymeric gel material Such functional groups include vinyl, substituted vinyl, or any group which upon cleavage yields a free radical, but for practical purposes a vinyl group is preferred because it is then possible to form the polymeric gel in the microcapillary and chemically bond it to the microcapillary wall simultaneously. Representative bifunctional reagents are 3-Methacryloxypropyltrimethoxysilane and 3-Methacryloxypropyl- dimethylethoxysilane, shown as (a) and (b) respectively below.

(a) $CH_2=C(CH_3)-CO_2-(CH_2)_3-Si(OCH_3)_3$

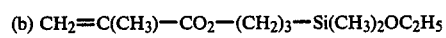

(b) $CH_2=C(CH_3)-CO_2-(CH_2)_3-Si(CH_3)_2OC_2H_5$

Other possible bifunctional reagents are vinyltriacetoxysilane, vinyltri($\beta$-methoxyethoxy)silane, vinyltrichlorosilane, and methylvinyldichlorosilane, this list being intended as illustrative but not exhaustive.

In the case of capillaries to which the bifunctional reagents do not bond, e.g., TEFLON, the capillaries may be employed without a connecting layer 14, or a layer of a polymer possessing reactive functional groups such as vinyl groups can be adsorbed onto the capillary wall and the polymeric gel 12 can then bind to this polymeric layer.

The hydrophilic polymers which are useful in the invention include polyoxides such as polyoxymethylene; polyethers such as polyethyleneoxide; polyalkylimines such as polyethyleneimine; polyamides such as polyacrylamide, polymethylacrylamide, poly-N,N-dimethylacrylamide, polyisopropylamide, and polyacrylylglycinamide; polyalkyleneglycols such as polyethylene glycol and polypropylene glycol; and polymers of vinylic materials such as polyvinyl alcohol, polyvinyl acetate and polyvinyl pyrrolidone. The molecular weight of the hydrophilic polymer is 4000–500,000 Daltons or higher, preferably in the range of approximately 8000 to 200,000 Daltons. The hydrophilic polymers are preferably linear polymers; helical hydrophilic polymers such as cellulose dextran, agarose, and xanthan gum have been found to function relatively poorly in the microcapillaries of the invention. The hydrophilic polymer is used at a concentration in the gel in the range of from about 1% weight/volume to about 40% weight/volume, preferably 5%-20% weight/volume, most preferably at about 5% weight/volume. Polyethylene glycol is a preferred hydrophilic polymer.

For the improved microcapillary in which polyethylene glycol is employed as a constituent of the polymeric gel, the polyethylene glycol used preferably has an average molecular weight of about 8000 Daltons or above, though material having an average molecular weight in the range 4000 to 35,000 Daltons will serve. Polyethylene glycol having an average molecular weight substantially lower than 4000 Daltons tends to form two phases with water at certain values of pH. Polyethylene glycol having an average molecular weight of about 8000 Daltons or above, on the other hand, forms homogeneous water solutions, and is therefore well-suited for use in the aqueous systems which are then employed in this invention.

For highest resolution it is necessary that at least the front end of the gel-containing microcapillary be cleanly and squarely cut perpendicular to the axis of the microcapillary. If the surface of the polymeric gel material which is exposed at the end of the microcapillary is uneven, it is impossible to make an injection of a uniform narrow band of sample, with the result that broad peaks are obtained. In practice, the end of the column can be conveniently cut cleanly and squarely perpendicular to the axis of the microcapillary by first forming a tight sheath of TEFLON or other plastic material around the end of the microcapillary and then cutting through this sheath and the microcapillary with a microtome. Alternatively, the end of the microcapillary may be scored carefully at a right angle to its axis by means of a sapphire cleaver, then broken cleanly by bending it.

The gel-containing microcapillaries of the invention are generally prepared as follows. First, the column is activated by heating it in excess of 100° C., generally for several hours, and then bringing its interior surface into contact with a basic material such as ammonia gas or a solution of a base In the heating step a temperature of 110° to 200° C. may be conveniently employed. The time of such heating can vary from a few hours to overnight or longer. In one procedure, the step of contacting with a basic material is accomplished by flushing the microcapillary with dry ammonia gas, generally for approximately 2 hours at a temperature in the range 20°-35° C., preferably at room temperature. In an alternative procedure, the column may be activated by heating it as above, then filling it with a solution of a base such as an alkali metal hydroxide, e.g. a 0.1N NaOH solution, leaving this solution in the microcapillary for approximately 1-2 hours at a temperature typically in the range 20°-35° C., preferably at room temperature, then flushing with water.

The time and temperature employed in activating the microcapillary are selected such that they are sufficient to activate the microcapillary so that good bonding between the microcapillary and the bifunctional reagent is achieved.

The activated microcapillary is then flushed with at least 100 tubing volumes of a solution of the bifunctional reagent to be employed in bonding the column gel to the tubing wall and then left to react for at least one hour and preferably 2 hours or longer at a temperature of 20°-35° C., preferably at room temperature, filled with this solution of bifunctional reagent. The solution of bifunctional reagent is prepared in a nonaqueous solvent such as an alcohol, an ether, or a moderately polar halogenated solvent and typically contains between 4 and 60% bifunctional reagent by volume. Representative solvents are methanol, dioxane, and methylene chloride. After the bifunctional reagent has been allowed to react with the inner wall of the microcapillary, excess unreacted bifunctional reagent is removed by rinsing the column with a suitable solvent such as methanol, followed by a further rinsing with water Typically at least 100 tubing volumes of solvent and water are employed.

Next, separate stock solutions of the monomers, cross-linkers, initiators, and free radical sources for the polymerization reaction are prepared, typically in 7 to 8 molar aqueous urea, though higher and lower concentrations of urea may be used. Gels which are intended to be non-denaturing are prepared without urea or other denaturing additives, and function well. The concentrations of these reagents are selected such that convenient aliquots of the solutions may be taken and mixed together to form a polymerization mixture having predetermined concentrations of monomer, crosslinker, and polymerization catalysts. Before mixing aliquots of these reagents together, the solutions are separately degassed for at least one hour. This degassing operation may be conducted in any of the several ways known to the art, but basically involves stirring the solutions mechanically or agitating them wit ultrasound while simultaneously applying a low vacuum of approximately 20 to 30 millimeters of mercury. The preparation of these solutions is as known to the art, for example, as shown by Hames and Rickwood.

For the preparation of the improved microcapillary containing polyethylene glycol according to one procedure, the polyethylene glycol is combined with degassed triply distilled water which has been cooled to about 10° C., then stirred while the temperature is raised slowly to room temperature. A clear transparent polyethylene glycol solution with no precipitate results. This solution is used to prepare the stock solutions of the buffer and other reagents to be employed in preparing the microcapillary If the polyethylene glycol is dissolved in warm water and the solution is cooled, a precipitate forms and the solution cannot be used.

The total concentration of monomer and the concentration of crosslinking agent in these sorts of systems are generally expressed respectively as %T and %C, employing the terminology of Hjerten. For the acrylamide/N,N'-methylenebisacrylamide system preferably employed in this invention, the definitions of %T and %C are given below.

$$\% T = \frac{\text{grams of acrylamide} + \text{grams of bisacrylamide}}{100 \text{ milliliters of solvent}}$$

$$\% C = \frac{\text{grams of bisacrylamide} \times 100}{\text{grams of bisacrylamide} + \text{grams of acrylamide}}$$

The concentrations of monomer and crosslinking agent are predetermined according to the porosity of the polymeric matrix desired. However, the concentrations of initiator and polymerization catalyst in the reaction mixture is generally best determined experimentally. This is done by preparing test solutions containing the desired %T and %C, but varying the amount of initiator and polymerization catalyst employed In the event that SDS-PAGE electrophoresis is contemplated, sodium dodecylsulfate is also included in the reaction mixture in the requisite amount. These test solutions are allowed to polymerize at the temperature at which the electrophoresis is to be performed and the progress of the polymerization reaction is monitored by ultraviolet spectroscopy by observing the decrease in the absorbance of the vinyl double bond. Alternatively, the microcapillary may be observed visually. Levels of initiator and polymerization catalyst are selected which cause the polymerization to be essentially complete in a reasonable time, such as approximately 45 to 60 minutes.

Once the correct reagent concentrations have thus been determined, a fresh mixture of the polymerization reagents is prepared and injected into the microcapillary tube, taking care not to create bubbles. For microcapillary columns containing a hydrophilic polymer such as polyethylene glycol, the hydrophilic polymer is included in the solution of polymerization reagents, as explained above. A small ID TEFLON tube is used to connect the microcapillary to the syringe employed to fill the microcapillary. When the microcapillary has been filled with polymerization mixture, the syringe is removed and both ends of the microcapillary are dipped in the "running" buffer, i.e., the buffer to be used for the electrophoresis, and maintained there while the polymerization reaction occurs.

The polymerization reaction is preferably carried out at the temperature which is to be employed for subsequent electrophoresis on the microcapillary column. While the polymerization reaction is occurring, the reaction is monitored separately in an aliquot of the reaction mixture by observing the loss of absorbance due to the vinyl groups by ultraviolet spectroscopy or visually. The polymerization reaction in the column and that in the separate monitor solution are the same. When the test solution indicates the polymerization reaction is essentially complete, which should be at a time between 45 and 60 minutes, the reaction is allowed to proceed for approximately another two hours, still maintaining the ends of the microcapillary in "running" buffer and maintaining the temperature as indicated above.

After the polymerization reaction in the microcapillary has gone essentially to completion, the microcapillary ends are removed from the "running" buffer and at least one of them is cut off cleanly and squarely. One way to accomplish this is to tightly sheath an end to be cut with small diameter TEFLON tubing. The TEFLON-sheathed ends of the microcapillary are then cut cleanly and squarely perpendicular to the axis of the microcapillary using a microtome, which cuts through the TEFLON sheathing, the microcapillary material, and the polymeric gel, leaving a very smooth surface of gel material exposed at the end of the microcapillary. Alternatively, the capillary may be scored and broken as discussed above. The end of the microcapillary which has been thus cut is examined under a microscope to ascertain that the cutting operation in fact produced the requisite flatness of the exposed polymeric gel. If necessary, further cuts can be made until a suitably flat end is produced. Both ends of the microcapillary are generally treated in this fashion, although it is really only necessary to have a square cut end on the front of the microcapillary.

Finally, the column is placed in suitable electrophoresis apparatus and a low electric field of approximately 100 to 150 V/cm is applied for a period of about one hour. If a very noisy baseline or a zero current condition is obtained, this indicates an improperly prepared column. In this event, a new microcapillary must be prepared.

In employing the gel-containing microcapillary column of the invention in electrophoresis, apparatus and techniques which are generally known to the those skilled in the art of open tube free-zone microcapillary electrophoresis are employed. See, for example, S. Terabe, et al., *Anal Chem.*, 56, 111–113 (1984); and J. W. Jorgenson and K. D. Lukacs, *Science*, 222, 266–272 (1983). In particular, the sample is preferably injected by the so-called "electrophoretic injection" technique, though other techniques known to the art can serve. Examples of such alternative injection techniques are syringe injection and isotachophoretic injection. In the electrophoretic injection technique, the front end of the electrophoresis microcapillary is dipped into a sample solution containing an electrode of the appropriate polarity and an electric field of approximately 50 to 100 V/cm is applied for a few seconds to cause electrophoresis of a small amount of the sample solution into the end of the microcapillary. The microcapillary is then transferred back to a solution of "running" buffer, the desired electrophoretic field is applied, and the electrophoresis is carried out in the normal way.

To aid in cooling the microcapillary, a cooling jacket or a related device is employed around the microcapillary over most of its length, excluding only the front and the rear ends of the microcapillary, which are respectively immersed in buffer solution and connected to the detector of the electrophoretic system. A cooling fluid such as $CCl_4$ is circulated through this jacket and maintained at whatever temperature is desired Alternatively, an electrically-controlled mechanical cooling device may be employed around the microcapillary column. Such "active" cooling is more effective in maintaining desired microcapillary temperatures than is air cooling.

A method of performing high resolution molecular sieving electrophoresis for analytical purposes thus includes the steps of injecting an aliquot of a sample containing analytes to be separated into a gel-containing microcapillary column of the invention, applying an electric field of between 400 and 1000 V/cm or higher, allowing a current typically less than about 40 microamperes to pass through the microcapillary, and instrumentally detecting and measuring the separated analytes sequentially as they migrate past the detector.

The gel-containing microcapillaries of the invention separate analytes as a function of the logarithms of their molecular weights in a linear fashion. Accordingly, it is possible to determine molecular weights of unknown analytes by comparing their mobilities under standard electrophoretic conditions with a calibration chart plotting the log of the molecular weight of standard materials versus the mobilities of such standard materials.

A method of determining the molecular weight of an analyte therefore is to prepare a gel-containing microcapillary column according to this invention, select standard values of the electrophoretic operating parameters, the applied field being typically between 400 and 1000 V/cm or higher and the current being typically less than about 50 microamperes, injecting onto this microcapillary column an aliquot of a standard solution containing several standard analytes of known molecular weight, applying the selected standard values of the electrophoretic operating parameters to the microcapillary column to separate the standards, measuring mobilities of the known standards under the conditions of the electrophoresis, plotting the log of the molecular weight for each of the standard materials versus its mobility under the standard operating conditions, electrophoretically analyzing an unknown solution on the same column under the same conditions, measuring the mobilities of the analytes contained therein, and finally determining the molecular weights of these analytes from a comparison with the calibration plot.

The improved microcapillary columns containing hydrophilic polymer additives are more easily and reproducibly prepared than similar columns not containing such additives, since the capillaries can be filled more readily with polymerization mixture without bubble formation, and the polymerization reaction occurs smoothly. The microcapillary columns of the invention also have longer shelf lives and better stability in use than columns not containing hydrophilic additives. Most importantly and unexpectedly, the improved microcapillary columns of the invention can be operated at exceptionally high field strengths, which permit exceptionally high resolution separations to be achieved in very short analysis times.

The following experimental preparations are intended as exemplary only, and are not intended to limit or define the scope of the invention.

EXPERIMENTAL SECTION

Acrylamide, N,N'-methylenebisacrylamide, N,N,N',N'-tetramethyleneethylenediamine (TEMED), ammonium persulfate, sodium dodecylsulfate, TRIS buffer, and disodium hydrogen phosphate were all ultrapure or electrophoretic grade materials obtained from Swartz/Mann Biotech of Cleveland, Ohio. Somewhat less pure acrylamide from other sources could be suitably purified by recrystallizing three times and deionizing it by treatment with ion exchange resin. Urea was freshly obtained, and triply recrystallized from water-methanol. Polyvinyl alcohol and polyvinylpyrrolidone were obtained from the Sigma Chemical Company, St. Louis, Mo.

Proteins and peptides were also obtained from the Sigma Chemical Company, and used as received. Recombinant human growth hormone (rhGH) and the related "two chain" material in which there is a proteolytic clip between amino acids 142 and 143 were obtained from Genentech. The bond cleavage between amino acids 142 and 143 of rhGH which forms the related "two chain" material does not cause the "two chain" material to break into two components since the disulfide bonds of rhGH remain intact.

Water was triply distilled and deionized. The polyethylene glycol was obtained either from Aldrich or Sigma and was of analytical reagent grade. The fused silica microcapillary tubing preferably employed in the invention was obtained from Scientific Glass Engineering Inc. This company also supplies such tubing in various dimensions. A sapphire cleaver useful in cutting off the ends of the microcapillaries was obtained from Ealing Electroptics Corp., 22 Pleasent Street, South Natick, Mass., 01760.

The narrow bore TEFLON tubing (0.2–0.25 millimeters ID) for filling microcapillary tube was obtained from S. Terabe of Kyoto University, Japan. All solutions were filtered through a nylon 66 or methylcellulose filter membrane having a 0.2 micrometer pore size. Analytical samples were kept frozen at $-20°$ C. prior to use, and aliquots of these samples for experimental work were stored at $-4°$ C. Proteins for SDS-PAGE work were prepared as known to the art.

A Soma S-3207 detector by Instrumentation for Research and Development, Inc., Kingston, Mass., was employed, and was modified for microcapillary work as described in the article by S. Terabe, et al, *Anal. Chem.*, 56. 111–113 (1984). Data were converted to digital form using a Nelson Analytical A/D Interface model 762 SA, and stored using an IBM PC/XT computer. Other equipment known to the art will also serve.

Preparation and Testing of Gel-Containing Microcapillary Having 10% T and Containing No Hydrophilic Polymer Additive Fused silica microcapillary tubing having an ID of 75 micrometers, a wall thickness of 30 micrometers, and a polyimide coating was employed. A 40 to 45 cm length of this tubing was taken for preparation of the gel-containing microcapillary. The polyimide coating was removed from a 1 cm section of one end of the tubing by burning. This end was ultimately connected to the detector of the electrophoresis apparatus.

The microcapillary tubing was heated overnight at about 120° C. in air, then flushed with dry ammonia gas at about 30° C. for approximately two hours. This and other operations reported herein as being carried out at about 30° C. were conducted at room temperature, which is generally about 30° C.±about 3° C. Next 100 μl of a 50% solution of 3-Methacryloxypropyltrimethoxysilane in methanol were passed through the microcapillary at a temperature of about 30° C., leaving the microcapillary filled with bifunctional reagent solution, the ends of the microcapillary were connected via a short length of TEFLON tubing (also filled with bifunctional reagent solution), and the closed and reagent-filled microcapillary was left overnight at about 30° C. The TEFLON tubing was then removed from one end of the microcapillary, and the microcapillary was flushed successively with 250 μl each of methanol and water to remove unreacted bifunctional reagent. The coated microcapillary was then installed in the detector of the electrophoresis apparatus. The treated microcapillary was cut to a length of somewhat greater than 20 cm, and a sheathing of TEFLON was installed on its "front" end.

Buffer solution was prepared by dissolving 1.1 g of TRIS buffer in 100 ml of 7 molar urea solution, adding 0.01 g of EDTA and 0.1 g of sodium dodecyl sulfate, and adjusting the pH to 8.6 by the addition of sodium dihydrogen phosphate.

A solution of acrylamide and N,N'-methylenebisacrylamide was prepared by combining 29 g of acrylamide and 1 g of N,N'-methylenebisacrylamide in 100 ml of buffer solution, giving a solution having a %T of 30% and a %C of 3.3%.

A solution of ammonium persulfate was prepared by dissolving 0.2 g of ammonium persulfate in 2 ml of the buffer solution.

The solutions of buffer, monomers, and ammonium persulfate were separately filtered through 0.2 micrometer filters and degassed for 2 hours by treating them with ultrasound while applying a vacuum of 20–30 mm of mercury.

Ten ml of the acrylamide-bisacrylamide solution was diluted to 30 ml with buffer solution, giving a final solution having %T=10% and %C=3.3%. One ml aliquots of this solution were experimentally treated with varying amounts of ammonium persulfate solution and TEMED, and polymerization times were monitored to determine the correct amounts of persulfate and TEMED to use. It was ascertained that addition of 2.5 µl of TEMED and 4 µl of the persulfate solution gave a polymerization time of about 45 minutes.

A 10 ml aliquot of the acrylamide-bisacrylamide solution was diluted to 30 ml with buffer solution, 2.5 µl of TEMED and 4 µl of ammonium persulfate solution were added, and in excess of 50 µl of this polymerization mixture were forced through the microcapillary until no bubbles were observed exiting the microcapillary. The injection syringe was carefully removed from the TEFLON tubing while continuing the injection, to prevent introduction of bubbles into the microcapillary. Finally, both ends of the microcapillary were immersed in "running" buffer and the polymerization was allowed to proceed at about 30° C. The polymerization of the remainder of the polymerization mixture was externally monitored. After polymerization appeared complete, the system was left for a further two hours or more to ensure full polymerization, then the microcapillary front end was cut off in a microtome at a microcapillary migration distance (front end to detector) of 20 cm. The final gel-containing microcapillary was evaluated for one hour under an applied field of 100 V/cm, and found to be satisfactory.

Figure 2:
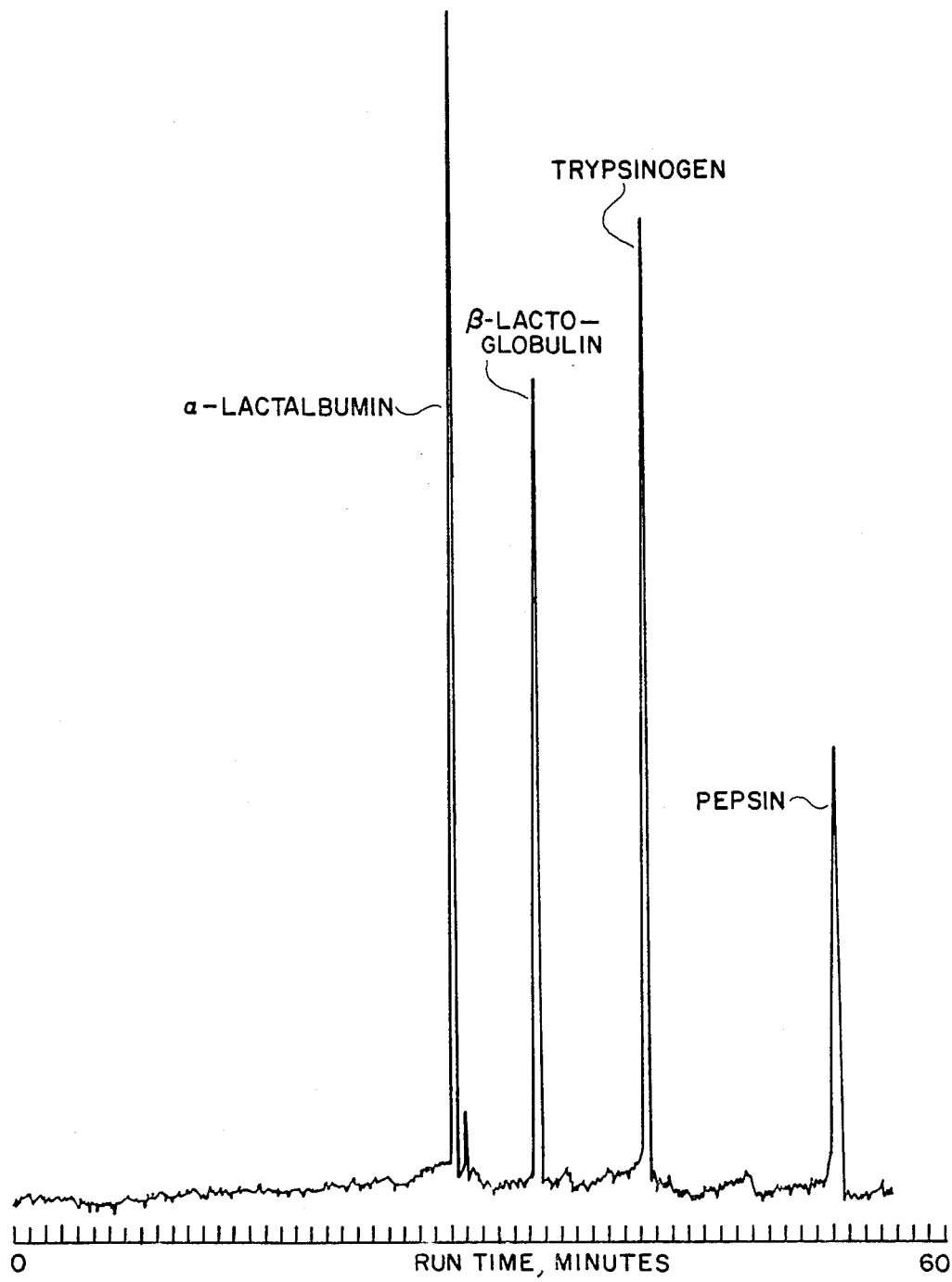
FIG. 2 shows an electropherogram of four standard proteins, $\alpha$-lactalbumin, $\beta$-lactoglobulin, trypsinogen, and pepsin on a gel-containing microcapillary column containing 10% total monomer, 3.3% crosslinker, but no added hydrophilic polymer; the pH of the buffer was 8.6, and electrophoresis was conducted under an applied field of 400 V/cm and a current of microamperes, over a 20 centimeter migration distance.

A mixture of four proteins, α-lactalbumin, β-lactoglobulin, trypsinogen, and pepsin, was prepared for SDS-PAGE electrophoresis in the standard manner known to the art, then a sample of this solution was electrophoretically injected onto the microcapillary column by application of an electrical field of 100 V/cm for 15 seconds. Electrophoresis was conducted at 400 V/cm and a current of 24 µA over the 20 cm migration distance. Results are shown in FIG. 2.

Figure 3:
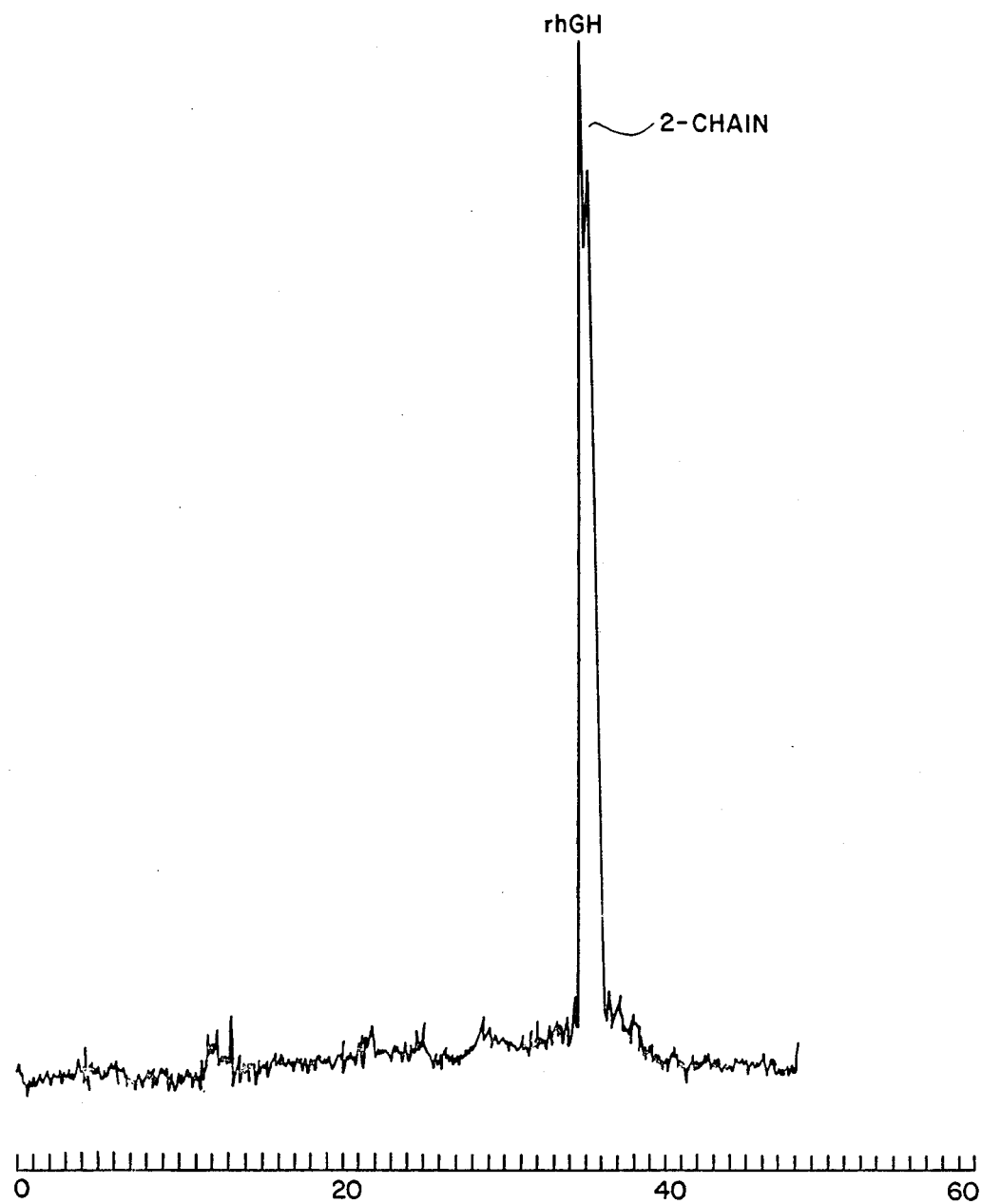
FIG. 3 shows an SDS-PAGE separation of recombinant human growth hormone (rhGH) and the related "two chain" material employing a microcapillary column and electrophoresis conditions employed in the separation shown in FIG. 2.

A mixture of recombinant human growth hormone (rhGH) and the corresponding "two chain" material was prepared for electrophoresis in the standard method known to the art, then a sample of this solution was electrophoretically injected into the microcapillary column by application of an electrical field of 100 V/cm and current of 6 µA for 60 seconds. Electrophoresis was conducted at 400 V/cm and a current of 24 µA over the 20 cm migration distance. Results are shown in FIG. 3.

Preparation and Testing of an Improved Microcapillary Containing 20% weight/volume of Polyethylene Glycol in the Polymeric Gel Matrix The same sort of fused silica microcapillary tubing as was employed in the work reported above was employed. This was preliminarily treated and reacted with bifunctional reagent as discussed above.

After coating the fused silica tubing with bifunctional reagent, the coated microcapillary was then installed in the detector of the electrophoresis apparatus.

Buffer solution was prepared by dissolving 3.025 g of TRIS buffer in 50 ml of 20% weight/volume polyethylene glycol 8000 in triply distilled water, and adjusting the pH to 8.0±0.1 by the addition of boric acid crystals. The polyethylene glycol solution was prepared as described above by combining the polyethylene glycol with cooled water, then stirring while warming the mixture slowly to room temperature.

A solution of acrylamide and N,N'-methylene-bisacrylamide was prepared by combining 14.5 g of acrylamide and 0.5 g of N,N'-methylene bisacrylamide in 50 ml of buffer solution, giving a solution having T of 30% and C=3.3%.

A solution of 10% ammonium persulfate was prepared by dissolving 0.2 g ammonium persulfate in 2 ml of the buffer solution.

All the solutions were filtered and degassed for at least 2 hours under a vacuum of 2–5 mm of mercury.

Two ml of the acrylamide-bisacrylamide solution was diluted to 10 ml with 20% weight/volume polyethylene glycol in triply distilled water giving a final solution having T=6%, C=3.3%. One ml aliquots of this solution were experimentally treated with varying amounts of ammonium persulfate solution and TEMED and the polymerization times were monitored to determine the correct amount of persulfate and TEMED to use. It was ascertained that addition of 3.0 µl of TEMED and 5 µl of the persulfate solution gave a polymerization time of about 45 minutes.

A 1.0 ml aliquot of the acrylamide-bisacrylamide diluted solution, 3 µl TEMED and 5 µl of ammonium persulfate solution were added, and more than of 50 µl of this polymerization mixture were forced through the microcapillary until no bubbles were observed exiting the microcapillary. The injection syringe was carefully removed while continuing the injection, to prevent introduction of bubbles into the microcapillary. Finally, both ends of the microcapillary were immersed in the "running" buffer and the polymerization was allowed to proceed at room temperature.

The final gel-containing microcapillary was evaluated for 4 days (24 hours/day) under an applied field of 926 V/cm and found to be satisfactory.

Figure 4:
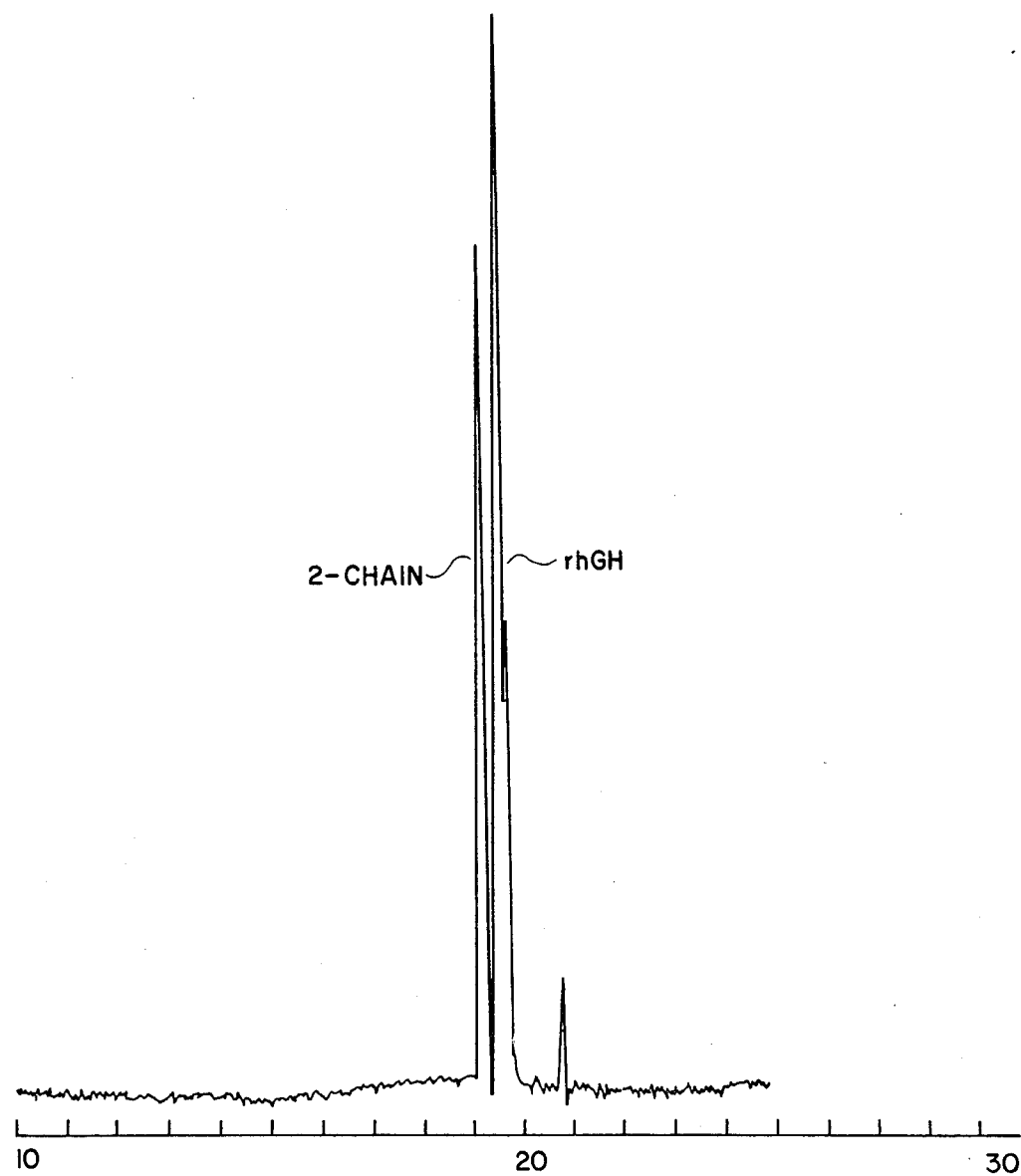
FIG. 4 shows an electrophoretic separation of rhGH and the corresponding "two chain" material on the improved microcapillary of the invention containing 20% polyethylene glycol 8000 but no SDS or urea, under an applied field of 926 V/cm. The sharp peaks of this electropherogram are clearly seen.

A mixture of recombinant human growth hormone (rhGH) and the corresponding "two chain" material was prepared for electrophoresis in the standard manner known to the art, then a sample of this solution was electrophoretically injected into the microcapillary column by application of an electrical field of 400 V/cm and current of 6 µA for 60 seconds Electrophoresis was conducted at 926 V/cm and current of 14 µA over the 12 cm migration distance. Results are shown in FIG. 4, where it is seen that an excellent separation between these extremely similar materials was achieved on the polyethylene glycol-containing microcapillary.

Preparation and Testing of an Improved Microcapillary Column Containing 5% Weight/Volume of Polyethylene Glycol in the Polymeric Gel Matrix A microcapillary column containing polyethylene glycol was prepared as above, except that polyethylene glycol having an average molecular weight of about 20,000 Daltons was employed, and the concentration of the polyethylene glycol in the gel was 5% weight/volume. Electrophoresis of a mixture of recombinant human growth hormone and the corresponding "two chain" material gave essentially the same separation as shown in FIG. 4, and in addition, higher sensitivity was achieved since the gel in this instance was clearer than in the column containing 20% weight/volume polyethylene glycol reported above.

Preparation of Improved Microcapillary Columns Containing Other Hydrophilic Polymers in the Polymeric Gel Matrix Two microcapillary columns approximately 50 cm in length and containing 5% weight/volume of polyvinyl alcohol and polyvinylpyrrolidone respectively in the gel were prepared in the same manner as detailed above for the columns containing polyethylene glycol. The average molecular weight of each polymer was approximately 40,000 Daltons. These columns were found to be quite easily prepared, and were additionally found to tolerate an applied field of 700 V/cm without damage, this field being the maximum field the power supply could provide across such relatively long columns. Although the two columns were actually tested under the above-recited conditions, higher fields of 1000 V/cm or more are considered possible with shorter columns, and it is also likely that the columns would survive under such high voltage for substantial periods.

Other embodiments of the invention will be apparent to those skilled in the art from a consideration of this specification or practice of the invention as disclosed herein. It is intended that the specification and examples be considered as exemplary only, with the true scope and spirit of the invention being indicated by the following claims.

What is claimed is:

1. A gel-containing microcapillary column for high precision and high performance electrophoresis, comprising:
   a microcapillary having an interior cavity and a wall with an inner surface;
   a crosslinked polymeric gel filling said interior cavity; and
   a hydrophilic polymer throughout said polymeric gel, at a level of 1–40% weight/volume;
   said microcapillary column being capable of being subjected to an electric field of at least 400 V/cm.

2. The microcapillary column of claim 1, further comprising:
   a layer of connecting material between said inner surface of said wall and said polymeric gel, said connecting material being covalently bonded to said microcapillary inner surface and to said polymeric gel.

3. The microcapillary of claim 2 wherein said connecting material is derived from a bifunctional reagent which possesses a reactive silane functional group capable of reacting with functional groups of said microcapillary inner surface, and a vinyl group capable of reacting with the monomer molecules which polymerize to form said gel.

4. The microcapillary of claim 3 wherein said bifunctional reagent is selected from the group consisting of 3-Methacryloxypropyltrimethoxysilane, 3-Methacryloxypropyldimethylethoxysilane, vinyltriacetoxysilane, vinyltri($\beta$-methoxyethoxy)silane, vinyltrichlorosilane, and methylvinyldichlorosilane.

5. The microcapillary column of claim 1 wherein said microcapillary is made of a silica-based material, alumina, beryllia, or TEFLON.

6. The microcapillary of claim 5 wherein said microcapillary is made of fused silica.

7. The microcapillary of claim 1 wherein said microcapillary has an internal diameter between 10 and 2000 micrometers.

8. The microcapillary of claim 1 wherein said microcapillary has a wall thickness in the range 25–400 micrometers.

9. The microcapillary of claim 1 wherein said polymeric gel further comprises a copolymer of acrylamide and at least one crosslinking agent.

10. The microcapillary of claim 9 wherein said crosslinking agent is selected from the group consisting of N,N'-methylenebisacrylamide, N,N'-(1,2-dihydroxyethylene)-bisacrylamide, N,N'-diallyltartardiamide, N,N'-cystamine-bisacrylamide, and N-acryloyltris(hydroxymethyl)aminomethane.

11. The microcapillary of claim 1 wherein said hydrophilic polymer is present in said polymeric ge at a level of 5–20% weight/volume.

12. The microcapillary of claim 1 wherein said hydrophilic polymer has an average molecular weight in the range 4000–500,000 Daltons.

13. The microcapillary of claim 1 wherein said hydrophilic polymer has an average molecular weight in the range 8000–200,000 Daltons.

14. The microcapillary of claim 1 wherein said hydrophilic polymer is polyethylene glycol.

15. The microcapillary of claim 14 wherein said polyethylene glycol has an average molecular weight in the range 4000–35,000 Daltons.

16. The microcapillary of claim 15 wherein said polyethylene glycol has an average molecular weight of at least approximately 8000 Daltons.

17. A method for preparing a gel-containing microcapillary column for high performance high precision electrophoresis, comprising:
   contacting the interior surface of a silica-based microcapillary with a basic material to activate said interior surface for reaction with a reagent possessing a silane functional group;
   treating said microcapillary with a first solution including a bifunctional reagent, said reagent possessing a reactive silane functional group capable of reacting with silanol groups, and a vinyl functionally capable of polymerizing with monomers, to cause covalent bonding of said reagent to the inner surface of the wall of said microcapillary via said reactive silane; and
   treating said microcapillary with a second solution including at least one monomer, at least one crosslinking agent, and at least one free radical source, to cause polymerization, with formation of a crosslinked polymeric gel filling the cavity of said microcapillary and covalent binding of said gel to said bifunctional reagent via said vinyl functionality, the resulting gel-filled microcapillary being capable of being subjected to an electric field of at least 400 V/cm.

18. The method of claim 17 further comprising the step of heating said microcapillary at a temperature in excess of 100° C. prior to said contacting step.

19. The method of claim 18 wherein said heating step is conducted at a temperature between 110° and 200° C.

20. The method of claim 17 wherein in said contacting step said basic material is ammonia gas and said contacting step further comprises flushing said microcapillary with said ammonia gas for a period of time sufficient to activate the inner surface of the microcapillary.

21. The method of claim 20 wherein said step of flushing with ammonia gas is conducted at a temperature in the range 20°–35° C.

22. The method of claim 17 wherein in said contacting step the basic material is a solution of an alkali metal hydroxide and said contacting step further comprises filling said microcapillary with said solution and maintaining said solution in said microcapillary for a period of time sufficient to activate the interior surface of the microcapillary.

23. The method of claim 22 wherein said contacting step is carried out at a temperature in the range 20°–35° C.

24. The method of claim 17 wherein said step of treating with a first solution including bifunctional reagent is conducted for at least one hour.

25. The method of claim 17 wherein said step of treating with a first solution including bifunctional reagent is conducted at a temperature in the range 20°–35° C.

26. The method of claim 17 further comprising the step of removing unreacted bifunctional reagent after the step of treating with a first solution including bifunctional reagent.

27. The method of claim 17 wherein in said step of treating with a second solution including monomer, crosslinking agent, and free radical source, said second solution is made up in the buffer to be employed in the electrophoresis, and is degassed.

28. The method of claim 17 wherein in said step of treating with a second solution of monomer, crosslinking agent, and free radical source, the concentrations of monomer and crosslinking agent in said second solution are predetermined and the concentration of free radical source is determined experimentally by varying the concentration of such free radical source in trial solutions and monitoring the polymerization reaction until a concentration of such free radical source is found which causes nearly complete polymerization to occur in approximately 45–60 minutes.

29. The method of claim 17 wherein said second solution further includes a hydrophilic polymer.

30. The method of claim 29 wherein said hydrophilic polymer is present in said second solution at a level of 1–40% weight/volume.

31. The method of claim 30 wherein said hydrophilic polymer is present in said second solution at a level of 5–20% weight/volume.

32. The method of claim 29 wherein said hydrophilic polymer has an average molecular weight in the range 4000–500,000 Daltons.

33. The method of claim 32 wherein said hydrophilic polymer has an average molecular weight in the range 8000–200,000 Daltons.

34. The method of claim 29 wherein said hydrophilic polymer is polyethylene glycol.

35. The method of claim 34 wherein said polyethylene glycol has an average molecular weight in the range 4000–35,000 Daltons.

36. The method of claim 35 wherein said polyethylene glycol has an average molecular weight of at least approximately 8000 Daltons.

37. The method of claim 17 wherein said bifunctional reagent is selected from the group consisting of 3-Methacryloxypropyltrimethoxysilane, 3-Methacryloxypropyldimethylethoxysilane, vinyltriacetoxysilane, vinyltri($\beta$-methoxyethoxy)silane, vinyltrichlorosilane, and methylvinyldichlorosilane.

38. The method of claim 17 wherein said solution of bifunctional reagent contains between 4% and 60% by volume of said reagent.

39. A method for performing high resolution molecular sieving electrophoresis, comprising:
   injecting an aliquot of a sample containing analytes to be separated onto a gel-containing microcapillary electrophoresis column comprising a microcapillary having an interior cavity and a wall with an inner surface, a crosslinked polymeric gel filling said interior cavity, and a hydrophilic polymer throughout said polymeric gel at a level of 1–40% weight/volume;
   applying to said microcapillary an electric field of at least 400 V/cm, to cause separation of said analytes on said microcapillary column; and
   instrumentally detecting and measuring the separated analytes sequentially.

40. A method for determining the molecular weight of an analyte, comprising:
   injecting an aliquot of a solution containing several standard analytes of known molecular weight onto a gel-containing microcapillary electrophoresis column comprising a microcapillary having an interior cavity and a wall with an inner surface, a crosslinked polymeric gel filling said interior cavity, and a hydrophilic polymer throughout said polymeric gel at a level of 1–40% weight/volume;
   applying to said microcapillary a preselected standard value electric field, said field being at least 400 V/cm, to cause separation of said standard analytes on said microcapillary column;
   instrumentally detecting each separated standard analyte; and measuring its mobility;
   plotting the log of the molecular weight for each standard analyte versus its mobility under the standard conditions to create a calibration plot; and
   electrophoretically analyzing a sample solution of analytes whose molecular weights are unknown on the same column under the same conditions, measuring the mobilities of analytes present in said sample solution, and determining the molecular weight of the analytes from the calibration plot.

* * * * *

UNITED STATES PATENT AND TRADEMARK OFFICE
CERTIFICATE OF CORRECTION

PATENT NO. : 4,865,707
DATED : September 12, 1989
INVENTOR(S) : Barry L. Karger

It is certified that error appears in the above-identified patent and that said Letters Patent is hereby corrected as shown below:

Column 6, line 16, "One en" should read --One end--.

Column 8, line 32, "them wit" should read --them with--.

Column 15, line 51, "groups of" should read --groups on--.

Column 16, line 14, "polymeric ge" should read --polymeric gel--.

Column 16, line 40-41, "functionally" should read --functionality--.

Signed and Sealed this

Twenty-fourth Day of August, 1993

Attest:

BRUCE LEHMAN

Attesting Officer     Commissioner of Patents and Trademarks